United States Patent
Li et al.

(10) Patent No.: US 9,623,111 B2
(45) Date of Patent: Apr. 18, 2017

(54) PEGYLATED ARTESUNATE DERIVATIVE, PHARMACEUTICAL COMPOSITION AND USE THEREOF

(71) Applicants: Institute of Pharmacology and Toxicology Academy of Military Medical Sciences PLA China, Beijing (CN); KPC PHARMACEUTICALS, INC., Kunming, Yunnan Province (CN)

(72) Inventors: Sicheng Li, Beijing (CN); Qingbin Meng, Beijing (CN); Junwen Mao, Beijing (CN); Jinfeng Li, Beijing (CN); An Xu, Beijing (CN); Jia Liu, Beijing (CN); Yuanjun Liang, Beijing (CN); Qiyan Jia, Beijing (CN); Jiufeng Yan, Beijing (CN); Xiaoyang Shen, Beijing (CN); Hui Liu, Beijing (CN); Na Xing, Beijing (CN)

(73) Assignees: KPC Pharmaceuticals, Inc., Yunnan Province (CN); Institute of Pharmacology and Toxicology Academy of Military Medical Science P.L.A. CHINA, Beijing (CN)

(*) Notice: Subject to any disclaimer, the term of this patent is extended or adjusted under 35 U.S.C. 154(b) by 0 days.

(21) Appl. No.: 14/899,138

(22) PCT Filed: Apr. 12, 2013

(86) PCT No.: PCT/CN2013/074114
§ 371 (c)(1),
(2) Date: Dec. 17, 2015

(87) PCT Pub. No.: WO2013/177978
PCT Pub. Date: Dec. 5, 2013

(65) Prior Publication Data
US 2016/0250339 A1 Sep. 1, 2016

(30) Foreign Application Priority Data
May 30, 2012 (CN) .......................... 2012 1 0173736

(51) Int. Cl.
*A61K 31/335* (2006.01)
*A61K 31/35* (2006.01)
*C07D 323/00* (2006.01)
*A61K 31/765* (2006.01)
*A61K 47/48* (2006.01)
*C08G 65/332* (2006.01)
*A61K 31/357* (2006.01)
*C08G 65/333* (2006.01)

(52) U.S. Cl.
CPC ...... *A61K 47/48215* (2013.01); *A61K 31/357* (2013.01); *A61K 31/765* (2013.01);
(Continued)

(58) Field of Classification Search
CPC .................................................... A61K 31/35
(Continued)

(56) References Cited

U.S. PATENT DOCUMENTS

2006/0046967 A1* 3/2006 Satyam ................ A61K 47/481
548/400

FOREIGN PATENT DOCUMENTS

| CN | 1903191 A | 1/2007 |
|---|---|---|
| CN | 102336904 A | 2/2012 |

OTHER PUBLICATIONS

Dec. 5, 2012—(WO) International Search Report and Written Opinion—App PCT/CN2013/074114—Eng Tran.
(Continued)

*Primary Examiner* — Shengjun Wang
(74) *Attorney, Agent, or Firm* — Banner & Witcoff, Ltd.

(57) ABSTRACT

A pegylated artesunate derivative, a pharmaceutical composition and uses thereof, the pegylated artesunate derivative is represented by the general formula (I):

(Continued)

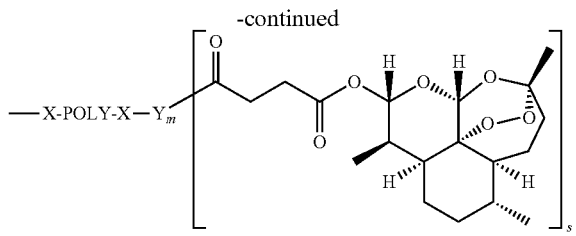

The pegylated artesunate derivative has activity comparable to that of artesunate, increased water solubility and stability, and an extended half-life in vivo.

20 Claims, 2 Drawing Sheets

(52) U.S. Cl.
CPC .......... *A61K 47/481* (2013.01); *C08G 65/332* (2013.01); *C08G 65/33396* (2013.01); *C08L 2203/02* (2013.01)

(58) Field of Classification Search
USPC ....... 514/450, 453; 549/348, 349; 424/78.37
See application file for complete search history.

(56) References Cited

OTHER PUBLICATIONS

Dec. 2, 2014—(WO) International Preliminary Report on Patentability—App PCT/CN2013/074114.

\* cited by examiner

PEGYLATED ARTESUNATE DERIVATIVE, PHARMACEUTICAL COMPOSITION AND USE THEREOF

CROSS-REFERENCE TO RELATED APPLICATIONS

This application is a U.S. National Stage application under 35 U.S.C. §371 of International Application PCT/CN2013/074114 (published as WO 2013/177978 A1), filed Apr. 12, 2013, which claims priority to Application CN 201210173736.X, filed May 30, 2012. Benefit of the filing date of each of these prior applications is hereby claimed. Each of these prior applications is hereby incorporated by reference in its entirety.

TECHNICAL FIELD

The present invention belongs to the field of pharmaceutical chemicals, and relates to a peglyated artesunate derivative, a pharmaceutical composition and uses thereof.

BACKGROUND ART

Artemisinin (as shown in the following Formula A) is a sesquiterpene lactone drug having hydroperoxy radical extracted from Chinese medicine *Artemisa apiacea*. Its effects on erythrocytic stage ultrastructure of rodent plasmodium are mainly change of membrane structure of plasmodium, and this drug first acts on endosome membrane, pellicle, mitochondria, endoplasmic reticulum, and on intranuclear chromatin in some extent. This suggests the action of artemisinin is mainly a function of interfering pellicle-mitochondria. It is possible that artemisinin acts on endosome membrane, thereby blocking the earliest stage of nutritional intake, quickly inducing amino acid starvation in plasmodia, rapidly forming autophagic vacuole, and eliminating continuously from polypide, so that plasmodia loss a lot of cytoplasm and die.

Formula A

Artemisinin is a high performance and quick acting antimalarial. It acts in plasmodium erythrocytic phase, is suitable for tertian malaria and malignant malaria, and especially has good effects for rescuing cerebral malaria. Its fever clearance time and time of turning plasmodium negative are shorter than chloroquine. It is also effective to chloroquine-resistant plasmodia.

After concluding and analyzing global anti-malaria work, World Health Organization (WTO) thinks drug-resistance may occur in plasmodia when artemisinin is simply used, and suggests artemisinin should not be simply used, but should be used in form of compound recipe. In the case of compound recipe of artemisinin, Dihydroartemisinin, Artesunate and Artemether have been developed.

Artesunate (as shown in the following Formula B) is suitable for rescue of patients of cerebral malaria and various dangerous and serious malarias, it is orally administered with a first dose of 100 mg, twice per day for the second day, 50 mg for each time, for consecutive 5 days. For intravenous injection, it should be added with 0.6 ml of accessional 5% sodium bicarbonate injection solution before clinical use, shaken for 2 minutes, diluted with 5.4 ml of 5% glucose injection solution or glucose-sodium chloride injection solution after complete dissolution, so 1 ml of solution contains 10 mg of artesunate for slow intravenous injection with a first dose of 1.2 mg/kg body weight, and the injection is repeated once 2, 24 and 48 hours after the first dose, respectively. For critical patients, the first dose can be doubled, and course of treatment can be 3 days.

Formula B

However, artesunate has drawbacks such as poor dissolubility, short action time, and high frequency of medication, so the research and development of artemisinin and derivatives are still focus for developing medicines for malaria treatment, especially derivatives with good water solubility and stable metabolism are drawing a lot of attentions.

Polyethylene glycol is a kind of artificially synthesized polymer with good biocompatibility and excellent water solubility and successfully applied to modify proteins, polypeptides and small molecular drugs. Artesunate coupled with polyethylene glycol not only has greatly improved water solubility, but also could achieve purpose of long-term action.

However, current PEG modification usually use monofunctional or difunctional linear molecules as structure choice. Actually, PEG modifiers are usually suitable for modification of proteins and polypeptides, while have obvious drawbacks such as small drug loading efficiency and high proportion of ineffective molecules when they are used for modifying small molecular drugs. On the other hand, derivatives of multivalent PEG modification can hardly be obtained, and the final product of modification may not have activity, that is, could be ineffective modification.

Hence, it is still in need to find new PEG molecule modified artesunate.

Contents of the Invention

With extensive studying and inventive works, the inventors of the present invention find that artesunate covalently modified with multivalent polyethylene glycol can maintain its activity, and the inventors further surprisingly find that its water solubility and stability are significantly improved, and particularly, its half-life in vivo is significantly extended. Thus, the present invention is provided.

One aspect of the present invention relates to an artesunate-polyethylene glycol derivative as shown in Formula (I), (I)

wherein,

POLY represents a polyethylene glycol residue with a molecular weight of 200 to 100,000 Da;

X represents amino or oxygen atom or methoxy;

Y represents a compound with amino acid structure containing two amino groups and one carboxyl, wherein the carboxyl together with X of POLY form an amide bond or ester bond, while multiple amino groups in the introduced distal end and the carboxyl of artesunate form amide bonds;

n and m represents polymerization degree of Y, m and n independently are an integer of 0 to 12;

r and s represents polymerization degree of artesunate; and when neither m nor n is 0, r and s separately are the double of n and m, and artesunate via carboxyl forms an amide bond with the multiple amino groups introduced by Y;

when m is 0 and n is not 0, or m is not 0 and n is 0, r and s separately are the double of n and m, and artesunate via carboxyl forms amide bonds with the multiple amino groups introduced by Y, and X at the end where m is 0 or n is 0 is methoxy; or when both m and n are 0, both r and s are 1, artesunate via carboxyl forms an ester or an amide with X.

The artesunate-polyethylene glycol derivative according to any one of items of the present invention, wherein Y is L-lysine, L-ornithine, 2,3-diaminopropionic acid, or 2,4-diaminobutyric acid.

The artesunate-polyethylene glycol derivative according to any one of items of the present invention, wherein m and n independently are 0, 1, 2 or 3.

The artesunate-polyethylene glycol derivative according to any one of items of the present invention, wherein the polyethylene glycol residue has a molecular weight of 2,000 to 40,000, for example, 10,000 to 30,000, 15,000 to 25,000, 18,000 to 22,000, 20,000, etc.

The artesunate-polyethylene glycol derivative according to any one of items of the present invention, which is shown in the following Formula (II), (II)

wherein, POLY and X are defined as any one of the above items.

The artesunate-polyethylene glycol derivative according to any one of items of the present invention, which is Compound 1: [(Artesunate-)$_2$-Lys-]$_2$-PEG$_{20k}$ (which structural formula is shown as Formula a), Formula a wherein, PEG$_{20k}$ represents PEG with molecular weight of 20 kD.

The artesunate-polyethylene glycol derivative according to any one of items of the present invention, which is shown as following Formula (III), (III)

wherein, POLY, Y, m and s are defined as any one of the above items, and n is 0, m is not 0.

The artesunate-polyethylene glycol derivative according to any one of items of the present invention, which is:

Compound 2: mPEG$_{20k}$-Lys-(Artesunate)$_2$ (which structural formula is shown as the following Formula b), Formula b wherein, mPEG$_{20k}$ represents mono-methoxy PEG with molecular weight of 20 kD;

or

Compound 3: mPEG$_{20k}$-Lys$_2$-(Artesunate)$_4$ (which structural formula is shown as the following Formula c), Formula c wherein, mPEG$_{20k}$ represents mono-methoxy PEG with molecular weight of 20 kD.

The artesunate-polyethylene glycol derivative according to any one of items of the present invention, which is shown as the following Formula (IV), (IV)

wherein, POLY and X are defined as any one of the above items, and m and n are both 0.

The artesunate-polyethylene glycol derivative according to any one of items of the present invention, which is:

Compound 4: Artesunate-NH-PEG$_{20k}$-NH-Artesunate (which structural formula is shown as the following Formula d), Formula d wherein, $PEG_{20k}$ represents PEG with molecular weight of 20 kD.

The inventors of the present invention used mice as experimental animals to observe the effects of derivatives of artesunate with different degrees of PEG modification on murine plasmodium blood symptom by murine malaria 4 day inhibition method, the results show that intraperitoneal injection of artesunate of 10 mg/kg body weight and artesunate-PEG modification derivative in equivalent molar dose can significantly inhibit development of murine plasmodium blood symptom with an inhibition rate of 80% or more, and there is no significant difference of inhibition rate between PEG derivative and artesunate in equivalent molar dose.

Normal rats are used to determine intracorporal process of drugs. The results show that single dose of caudal vein injection of Compound 1 (corresponding to artesunate of 10 mg/kg) can obtained a extended drug-time curve, and half-life is extended by about 5 times. The compounds of the present invention (including Compounds 1-4) show significant effects of extending half-life.

Another aspect of the present invention relates to a method for preparing the artesunate-polyethylene glycol derivative according to any one of the items of the present invention, comprising the following steps:

placing artesunate and a multivalent polyethylene glycol modifier with free amino groups in an inert solvent, performing a coupling reaction between a carboxyl of artesunate and an amino or hydroxyl of multivalent polyethylene glycol modifier in the presence of catalysis of a coupling agent and an organic alkali.

The preparation method according to any one of items of the present invention, characterized in any one or more of the following items:

(1) the polyethylene glycol modifier is $mPEG_{20k}$ or $[Lys-]_2-PEG_{20k}$;
(2) the inert solvent is selected from dichloromethane, chloroform, toluene, or dimethylformamide (DMF);
(3) the coupling agent is selected from N-ethyl-N'-(3-dimethylaminopropyl)carbodiimide hydrochloride (EDC), 1,3-diisopropylcarbodiimide (DIC), N,N-dicyclohexylcarbodiimide (DCC);
(4) the reaction temperature is controlled at 0-25° C.;
(5) the organic alkali is selected from the group consisting of pyridine, triethylamine and diisopropylethylamine.

Further another aspect of the present invention relates to a pharmaceutical composition, which comprises the artesunate-polyethylene glycol derivative according to any one of the items of the present invention; optionally, further comprises a pharmaceutically acceptable carrier or excipient.

Usually, the pharmaceutical composition of the present invention comprises 0.1-90 wt % of the compound of the present invention (i.e., artesunate-polyethylene glycol derivative). The pharmaceutical composition can be prepared by a known method in the art. For this purpose, the compound can be combined with one or more solid or liquid pharmaceutically acceptable excipient and/or adjuvant, and processed to be an administration form or dosage form suitable for human uses.

The compound or pharmaceutical composition containing the compound can be administered in a unit dosage form, and administration routes can be intestinal route or parenteral route, such as oral, intramuscular, subcutaneous, intranasal, buccal, percataneous, peritoneal, rectal routes. The dosage form can be tablets, capsules, dripping pills, aerosols, pills, powders, solutions, suspensions, emulsions, granules, liposomes, transdermal agents, buccal tablets, suppositories, freeze-dried powder injections. It can be normal preparations, or sustained release preparations, controlled release preparations as well as various particulate delivery systems. In order to obtain tablets as unit dosage form, various carriers known in the art can be used. The examples of carriers are, such as, diluents and absorbers, such as starch, dextrin, calcium sulfate, lactose, mannitol, sucrose, sodium chloride, glucose, urea, calcium carbonate, kaolin, microcrystalline cellulose, aluminum silicate; wetting agents and binders, such as water, glycerol, polyethylene glycol, ethanol, propanol, starch paste, dextrin, syrup, honey, glucose solution, acacia mucilage, gelatin paste, sodium carboxymethylcellulose, shellac, methylcellulose, potassium phosphate, polyvinylpyrrolidone; disintegrants, such as dry starch, alginate, agar powder, laminarin powder, sodium hydrogen carbonate and citric acid, calcium carbonate, polyoxyethylene, sorbitol fatty acid esters, sodium dodecyl sulfate, methylcellulose, ethylcellulose; disintegration inhibitors, such as sucrose, tristearin, cacao butter, hydrogenated oil; absorption enhancers, such as quaternary ammonium salt, sodium dodecyl sulfate; lubricants, such as talc powder, silica, corn starch, stearates, boric acid, liquid paraffin, polyethylene glycol. The tablets can be further processed to form coated tablets, such as sugar coated tablets, thin membrane coated tablets, enteric-coated tablets, or double layer tablets or multiple layer tablets. In order to obtain pills as unit dosage form, various carriers known in the art can be used. The examples of these carriers can be, such as diluents and absorbers, such as glucose, lactose, starch, cacao butter, hydrogenated oil, polyvinylpyrrolidone, Gelucire, kaolin, talc powder; binders such as acacia gum, tragacanth gum, gelatin, ethanol, honey, liquid sugar, rice paste or panada; disintegrants, such as agar powder, dry starch, alginates, sodium dodecyl sulfate, methylcellulose, ethylcellulose. In order to obtain suppositories as unit dosage form, various carriers known in the art can be used. The examples of these carriers are, such as polyethylene glycol, lecithin, cacao butter, fatty alcohols, esters of fatty alcohols, gelatin, semi-synthesized glycerides. In order to obtain capsules as unit dosage form, the compound of Formula I or a stereoisomer thereof as effective component is blended with various carriers, and the resultant mixture is placed in a hard gelatin capsule or a soft capsule. The compound of Formula I or a stereoisomer thereof as effective component can also be processed to obtain microcapsules, suspended in aqueous medium to obtain a suspension, or loaded in hard capsules or processed to obtain injections. In order to obtain injections as unit dosage form, such as solutions, emulsions, freeze-dried injection powders or suspensions, all diluents commonly used in the art can be used, such as, water, ethanol, polyethylene glycol, 1,3-propanediol, ethoxylated isostearyl alcohol, multiple-oxidized isostearyl alcohol, polyoxyethylene sorbitan fatty acid ester. In addition, in order to obtain iso-osmia injections, a suitable amount of sodium chloride, glucose or glycerol can be added to injection preparation. Furthermore, conventional co-solvents, buffering agents, pH regulators and so on can also be added.

In addition, if desired, coloring agents, preservatives, perfumes, correctants, sweet tastes or other materials can be added to the pharmaceutical preparations.

The administration dose of the compound of the present invention depends on many factors, such as property and severity of disease to be prevented or treated, gender, age, body weight and individual response of patient or animal, the specific compound to be used, administration route and times, etc. The above dose can be administrated via single dose form or several, such as 2, 3 or 4, dosage forms.

The term "composition" used in the text refers to a product comprising designated amounts of designated components, and any product directly or indirectly derived from a combination of designated amounts of designated components.

The actual dose levels of various active components in the pharmaceutical composition of the present invention can be changed so that the active compounds are in effective levels for specific patients, and desired therapeutic effects can be achieved with the compositions and the administration routes. Dosage level can be determined according to activity of specific compound, administration route, severity of disease to be treated, and conditions and medical history of patient. However, a method in the art comprises starting a dose of compound that is lower than the level as required for achieving desired therapeutic effects, gradually increasing the dose until desired effects are achieved.

The further another aspect of the present invention relates to use of the artesunate-polyethylene glycol derivative according to any one of the items of the present invention in the manufacture of a medicament for combating plasmodium, or a medicament for prophylaxis and/or treatment of a disease caused by a plasmodium such as malaria.

The further another aspect of the present invention relates to a method for combating plasmodium in vivo or in vitro, comprising a step of using an effective amount of the artesunate-polyethylene glycol derivative according to any one of the items of the present invention.

The further another aspect of the present invention relates to a method for prophylaxis and/or treatment of a disease caused by a plasmodium such as malaria, comprising a step of using an effective amount of the artesunate-polyethylene glycol derivative according to any one of the items of the present invention.

In the aforementioned treatment and/or prophylaxis or aid therapy, the compound of the present invention in a therapeutically and/or prophylactically effective amount can be used in form of pure compound, or in form of pharmaceutically acceptable ester or prodrug thereof (if they exist). Alternatively, the compound can be administered via a pharmaceutical composition comprising the compound and one or more pharmaceutically acceptable excipients. The term the compound of the present invention in "therapeutically and/or prophylactically effective amount" means that the compound is in an amount sufficient to achieve prophylactically and/or therapeutically reasonable ratio of effect/risk. It should be understood that the total amount per day of the compound or composition of the present invention must be determined by a physician within the range of reliable medical decisions. As for any specific patients, the specific therapeutically amount must be determined based on various factors, including the diseases to be treated and severity thereof, the activity of the used specific compound, the used specific composition, the age, body weight, general health status, gender and food of patient, the administration time and route and excretory rate of the used specific compound, the drug(s) administered in combination or simultaneously with the specific compound, and similar factors well known in the art of medicine. For example, it is a common method in the art to increase gradually the dose of compound from a level lower than that for achieving desired therapeutic effects to a level enough to achieve the desired therapeutic effects. In general, the dose of the compound of Formula I of the present invention for mammals especially human can be 0.001-1000 mg/kg body weight per day, such as 0.01-100 mg/kg body weight per day, 0.01-10 mg/kg body weight per day.

The compounds of the present invention can effectively prevent and/or treat the diseases or disorders as mentioned in the present invention.

The compounds as mentioned in the present invention, if not specifically explained, refer to the artesunate-polyethylene glycol derivatives of the present invention.

In the present invention, the term "effective amount" refers to a dose that can achieve treatment, prophylaxis, alleviation and/or remission of the diseases or disorders as mentioned the present invention.

The term "subject" refers to a patient or other animals, especially mammals, such as human, dog, monkey, cattle, horse, etc., which take the compound of the present invention for treatment, prophylaxis, alleviation and/or remission of diseases or disorders as mentioned in the present invention.

The term "disease and/or disorder" refers to a physical condition of the subject, and the physical condition relates to the diseases and/or disorders as mentioned in the present invention.

Some abbreviations in the present invention have the following meanings.

PEG polyethylene glycol

Artesunate arteannuinum succinate

BOC t-butyloxycarboryl

Lys lysine

DCC dicyclohexylcarbodiimide

NHS N-hydroxysuccimide

TFA trifluoroacetic acid

Other abbreviations not indicated here have meanings well known in the art.

Beneficial Effects of the Invention

The peglyated derivatives of artesunate, their pharmaceutical compositions have activity equivalent to that of artesunate, their water solubility and stability are significantly improved, and their half-life in vivo are significantly extended.

SPECIFIC MODELS FOR CARRYING OUT THE INVENTION

Some embodiments of the present invention are described in details in conjunction with the following examples, but those skilled in the art would understand these examples are merely used to illustrate the present invention, rather than to restrict the scope of the present invention. Those not specifically explained conditions in the examples are carried out according to conventional conditions or conditions recommended by manufacturers. Those reagents or instruments without giving manufacturers are all conventional products commercially available in markets.

Diaminopolyethylene glycol and mono-methoxy-aminopolyethylene glycol were products of Beijing Kaizheng Company, and 1-ethyl-3-(3-dimethylaminopropyl)carbodiimide hydrochloride (EDC.HCl) and dimethylaminopyridine (DMAP) were domestic analytic reagents. Artesunate was raw material commercially available in markets.

EXAMPLE 1

Compound 1: Preparation of [(Artesunate-)$_2$-Lys-]$_2$-PEG$_{20k}$

Formula a 20.0 g (1 mmol) of PEG$_{20K}$-(NH2)$_2$ and 1.04 g (3 mmol) of BOC-Lys(BOC)-OH were dissolved in 100 ml of dichloromethane, 0.618 g (MW: 206, 3 mmol) of DCC, 0.445 g (3 mmol) of N-hydroxysuccinimide were added at 0° C., stirred for 30 min; reaction was performed at room temperature of 25° C. under stirring for 2 hours, and then terminated; the precipitate was removed by filtration, the filtrate was concentrated to dry, precipitated with ethyl ether, and dried naturally; the dry product was dissolved in 100 ml of TFA/DCM (V/V: 1/3), stirred at room temperature of 25° C. for 2 hours, to remove BOC protecting group; concentrated under vacuum to dry, added with 200 ml of sodium hydroxide aqueous solution (M/M: 4/96) for dissolution, added with a suitable amount of sodium chloride, extracted with dichloromethane for 3 times, the organic phases were combined, dried with anhydrous sodium sulfate, concentrated under vacuum to dry, precipitated with ethyl ether, dried under vacuum to constant weight. 18.2 g of dry product was weighed, dissolved in 90 ml of dichloromethane, added with 2.3 g (6 mmol) of Artesunate, added with 1.2 g (6 mmol) of DCC, 0.69 g (6 mmol) of N-hydroxysuccinimide at 0° C., stirred for 30 min; reaction was performed at room temperature of 25° C. under stirring for 2 hours, then terminated; the precipitate was removed by filtration, the filtrate was concentrated to dry, precipitated with ethyl ether, dried naturally, to obtain dry product of 17.5 g, yield 87.5%. NMR(CDCL3,300 MHz): δ0.94 (s,12H, C9-CH3), 0.95(s, 12H, C6-CH3), 1.44(s,12H, C3-CH3), 1.5-1.8(bs,CH2 (lysαβγ)), 2.68 (m, 4H, H-9), 3.63(bs,1868H, PEG main chain), 5.44(s,4H, H-12).

EXAMPLE 2

Compound 2: Preparation of mPEG$_{20K}$-(Artesunate)$_2$

Formula b

20.0 g (1 mmol) of mPEG$_{20K}$-NH$_2$ and 0.52 g (1.5 mmol) of BOC-Lys(BOC)-OH were dissolved in 100 ml of dichloromethane, 0.309 g (1.5 mmol) of DCC, 0.223 g (1.5 mmol) of N-hydroxysuccinimide were at 0° C., stirred for 30 min; reaction was performed at room temperature of 25° C. under stirring for 2 hours, then terminated; the precipitate was removed by filtration, the filtrate was concentrated to dry, precipitated with ethyl ether, dried naturally; the dry product was dissolved in 100 ml of TFA/DCM (V/V: 1/3), stirred at room temperature of 25° C. for 2 hours, to remove BOC protecting group; concentrated under vacuum to dry, added with 200 ml of sodium hydroxide aqueous solution (M/M: 4/96) for dissolution, added with a suitable amount of sodium chloride, extracted with dichloromethane for 3 times, the organic phases were combined, dried with anhydrous sodium sulfate, concentrated under vacuum to dry, precipitated with ethyl ether, dried under vacuum to constant weight; 18.8 g of dry product was weighed and dissolved in 95 ml of dichloromethane, added with 1.15 g (MW: 384.42, 3 mmol) of Artesunate, 0.62 g (3 mmol) of DCC, 0.35 g (3 mmol) of N-hydroxysuccinimide at 0° C., and stirred for 30 min; reaction was performed at room temperature of 25° C. for 2 hours, then terminated; the precipitate was removed by filtration, the filtrate was concentrated to dry, precipitated with ethyl ether, dried naturally, to obtain dry product of 18.1 g, yield 90.5%. NMR (CDCL3,300 MHz): δ0.94 (s,6H, C9-CH3), 0.95(s,6H, C6-CH3), 1.44(s,6H, C3-CH3), 1.5-1.8(bs,CH2 (lysαβγ)), 2.68 (m, 2H, H-9), 3.15 (s,3H,CH3-OPEG), 3.63(bs,1824H, PEG main chain), 5.44(s,2H, H-12).

EXAMPLE 3

Compound 3: Preparation of mPEG$_{20k}$-Lys$_2$-(Artesunate)$_4$

20.0 g (1 mmol) of mPEG$_{20K}$-NH$_2$ and 0.52 g (1.5 mmol) of BOC-Lys(BOC)-OH were dissolved in 100 ml of dichloromethane, 0.309 g (1.5 mmol) of DCC, 0.223 g (1.5 mmol) of N-hydroxysuccinimide at 0° C., stirred for 30 min; reaction was performed at room temperature of 25° C. for 2 hours, then terminated; the precipitate was removed by filtration, the filtrate was concentrated to dry, precipitated with ethyl ether, dried naturally; the dry product was dissolved in 100 ml of TFA/DCM (V/V: 1/3), stirred at room temperature of 25° C. for 2 hours to remove BOC protecting group; concentrated under vacuum to dry, added with 200 ml of sodium hydroxide aqueous solution (M/M: 4/96) for dissolution, added with a suitable amount of sodium chloride, extracted with dichloromethane for 3 times, the organic phases were combined, dried with anhydrous sodium sulfate, concentrated under vacuum to dry, precipitated with ethyl ether, dried under vacuum to constant weight; the dry product and 1.04 g (3 mmol) of BOC-Lys(BOC)-OH were dissolved in 100 ml of dichloromethane, 0.618 g (3 mmol) of DCC, 0.445 g (MW: 115, 3 mmol) of N-hydroxysuccinimide at 0° C., stirred for 30 min; reaction was performed at room temperature of 25° C. for 2 hours, then terminated; the precipitate was removed by filtration, the filtrate was concentrated to dry, dried naturally; the dry product was dissolved in 100 ml of TFA/DCM (V/V: 1/3), stirred at room temperature of 25° C. for 2 hours to remove BOC protecting group; concentrated under vacuum to dry, added with 200 ml of sodium hydroxide aqueous solution (M/M: 4/96) for dissolution, added with a suitable amount of sodium chloride, extracted with dichloromethane for 3 times, the organic phases were combined, dried with anhydrous sodium, concentrated under vacuum to dry, precipitated with ethyl ether, dried under vacuum to constant weight; 17 g of dry product was weighed, dissolved in 85 ml of dichloromethane, added with 2.3 g (6 mmol) of Artesunate, 1.2 g (6 mmol) of DCC, 0.69 g (6 mmol) of N-hydroxysuccinimide at 0° C., stirred for 30 min; reaction was performed at room temperature of 25° C. under stirring for 2 hours, then terminated; the precipitate was removed by filtration, the filtrate was concentrated to dry, precipitated with ethyl ether, naturally dried, to obtain dry product of 16 g, yield 80%. NMR (CDCl3,300 MHz): δ0.94 (s,12H, C9-CH3), 0.95(s,12H, C6-CH3), 1.44 (s, 12H, C3-CH3), 1.5-1.8(bs, CH2 (lysαβγ)), 2.68(m,4H, H-9), 3.15 (s, 3H, CH3-OPEG), 3.63 (bs, 1824H, PEG main chain), 5.44(s,4H, H-12).

Formula c

EXAMPLE 4

Compound 4: Preparation of Artesunate-NH-PEG$_{20k}$-NH-Artesunate

Formula d 20 g of PEG$_{20K}$-(NH2)$_2$ was dissolved in 100 ml of dichloromethane, added with 1.15 g (MW: 384.42, 3 mmol) of Artesunate, 0.618 g (MW: 206, 3 mmol) of DCC, 0.35 g (MW: 115, 3 mmol) of NHS at 0° C., stirred for 30 min; reaction was performed at room temperature of 25° C. under stirring for 2 hours, then terminated; the precipitate was removed by filtration, the filtrate was concentrated to dry, precipitated with ethyl ether, dried naturally, to obtain dry product of 19.2 g, yield 96%. NMR (CDCL3,300 MHz): δ0.94 (s,6H, C9-CH3), 0.95 (s,6H, C6-CH3), 1.44 (s, 6H, C3-CH3), 1.5-1.8 (bs,CH2 (lysαβγ)), 2.68(m,2H, H-9), 3.63 (bs,1868H, PEG main chain), 5.44(s,2H, H-12).

EXAMPLE 5

Determination of Drug-Time Curve In Vivo

Samples: Artesunate, Compounds 1-4.

Preparation of samples: artesunate was dissolved with 5% NaHCO$_3$ physiological saline to obtain 10 mg/ml colorless pellucid solution; Compound 1 was dissolved with injection physiological saline to prepare a colorless pellucid solution containing equivalently 10 mg/ml artesunate.

Animals: SD rats were purchased from the Animal Center of the Military Medical Science Academy of the PLA, body weight 200±10 g, male, conventionally raised, free diet.

Experimental method: solutions of artesunate and Compound 1 samples were administrated to each rat by intravenous injection in an amount of 0.2 ml (a dose equivalent to 10 mg/kg artesunate). Blood samples were collected at 0 min, 10 min, 20 min, 30 min, 45 min, 1 hr, 1.5 hr, 2 hr, 2.5 hr, 3 hr, 4 hr, 6 hr, 8 hr, 10 hr, respectively, and serum concentration of dihydroartemisinin were measured by LC-MS method.

Experimental Results: See FIG. 1.

Figure 1:
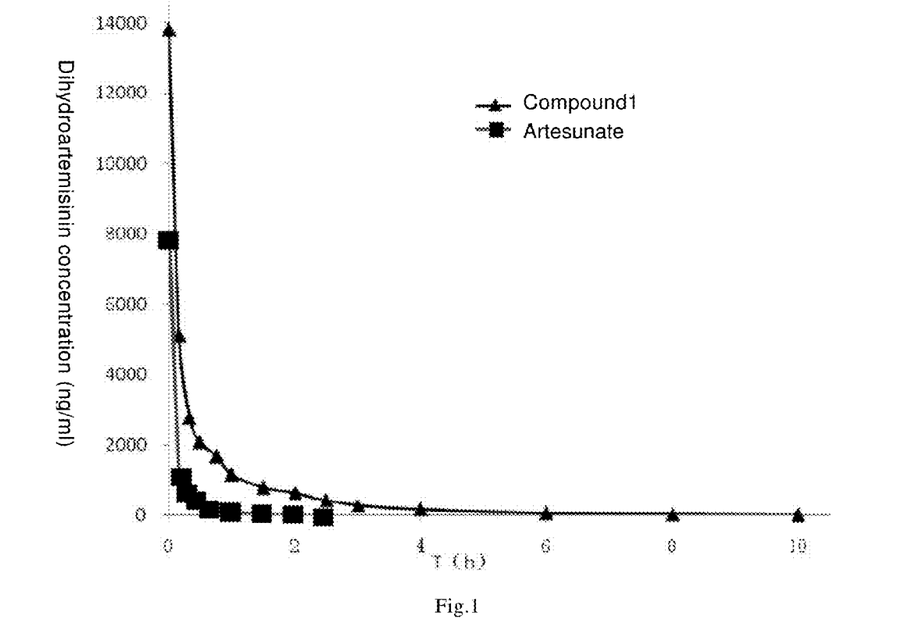
FIG. 1: shows drug-time curve of dihydroartemisinin after administration, in which dihydroartemisinin comprises Compound 1 and normal artesunate.

The results showed that in comparison with artesunate, Compound 1 obtained an extended drug-time curve, which half-life was extended by about 5 times.

The half-life values of Compounds 2-4 were significantly extended as well.

EXAMPLE 6

Evaluation of Anti-Malarial Effects

Samples: Artesunate, Compound 1, Compound 2, Compound 3, Compound 4.

Preparation of samples: artesunate was dissolved with 5% NaHCO$_3$ physiological saline to form 2.5 mg/ml colorless pellucid solution; Compound 1, Compound 2, Compound 3 were dissolved with physiological saline to form colorless pellucid solutions containing equivalently 2.5 mg/ml artesunate (respectively, 9.3 mg/ml, 19.1 mg/ml, 35.2 mg/ml);

Compound 4 was dissolved with injection physiological saline to form a colorless pellucid solution containing equivalently 1 mg/ml artesunate (27.2 mg/ml).

Preparation of animals and pathological models: Kunming mice were purchased from the Animal Center of the Military Medical Science Academy of the PLA, body weight 20±2 g, female, conventionally raised, free diet. The mice were inoculated 1×10$^7$ plasmodia via intraperitoneal injection on the test day (DO) to infect red blood cells to establish murine malaria infection models.

Dosage regimen: the solutions of artesunate and PEGlyation derivatives thereof were diluted with injection water to a concentration equivalent to 1 mg/ml artesunate, and each mouse was administrated by 0.2 ml intraperitoneal injection (a dose equivalent to 10 mg/kg artesunate). First administration was performed 3 hours after the mice were infected, then administrated once per 24 hours, until the 3$^{rd}$ day (D3) after infection, that was, totally administrated for 4 times. The placebo control group was injected with physiological saline of same volume.

Experimental Results:

a) the intraperitoneal injection of artesunate and its PEGlyation derivatives could significantly inhibit the development of Parasitemia in mice infected with *Plasmodium berghei*.

Figure 2:
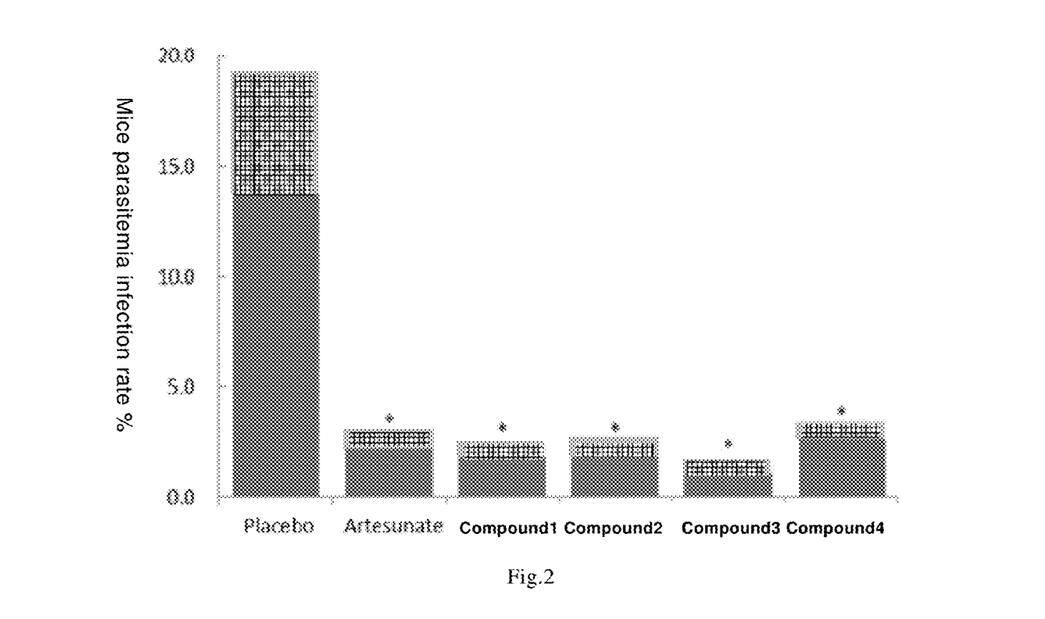
FIG. 2: shows effects of artesunate and pegylation derivatives thereof on inhibiting plasmodium blood symptom in murine malaria models, *P<0.01, in which black filled markers represent mean value (Mean); mesh filled markers represent standard deviation (STD).

On the 4$^{th}$ day (D4) after administration, the Placebo control group had a mean plasmodia parasitic rate of 13.7%, while 10 mg/kg body weight artesunate and equivalent dose of the PEGlyation derivatives intraperitoneal injection groups had similar mean plasmodia parasitic rates of merely 0.4-2.6%, and were significantly different from that of the control group (P<0.01), which indicated that all test samples had significantly activity of combating malaria (see: FIG. 2).

b) the intraperitoneal injection of artesunate and its PEGlyation derivatives could significantly inhibit the development of Parasitemia in mice infected with *Plasmodium berghei*.

On the 4$^{th}$ day (D4) after administration of 10 mg/kg body weight artesunate and its PEGlyation derivatives, their inhibition rates to *Plasmodium berghei* were all 80% or more, and there was no significant difference of inhibition rate between the derivatives and artesunate (Table 1). It could be seen that the different PEGlyation modification degrees showed no significant effect on anti-malarial activity of artesunate under this dose.

TABLE 1

Comparison of inhibition rates to *Plasmodium berghei* between artesunate and its PEGlyation derivatives

| Test sample | Number of mice | Parasitemia (%) Mean | STD |
|---|---|---|---|
| Artesunate | 5 | 84.0(76.0-94.6) | 6.1 |
| Compound 1 | 6 | 87.2(82.7-92.7) | 4.0 |
| Compound 2 | 5 | 87.0(79.3-97.4) | 6.6 |
| Compound 3 | 4 | 92.1(87.8-95.1) | 3.0 |
| Compound 4 | 4 | 80.8(79.7-87.0) | 6.0 |

Although the specific models of the present invention have been described in details, those skilled in the art would understand according the disclosed teachings, these details could be changed or replaced, and all these changes are fallen into the protection scope of the present invention. The total scope of the present invention is given by the appended claims and any equivalents thereof.

What is claimed is:

1. An artesunate-polyethylene glycol derivative as shown in Formula (I), (I)

-continued wherein,
POLY represents a polyethylene glycol residue with a molecular weight of 200 to 100,000 Da;
X represents amino or oxygen atom or methoxy;
Y represents a compound with amino acid structure containing two amino groups and one carboxyl, wherein the carboxyl together with X of POLY form an amide bond or ester bond, while the multiple amino groups in the introduced distal end and the carboxyl of artesunate form amide bonds;
n and m represent polymerization degree of Y, and m and n independently are 0 or 1;
r and s represents polymerization degree of artesunate; and
when neither m nor n is 0, r and s separately are the double of n and m, and artesunate via carboxyl forms an amide bond with the multiple amino groups introduced by Y;
when m is 0 and n is not 0, or m is not 0 and n is 0, r and s separately are the double of n and m, and artesunate via carboxyl forms amide bonds with the multiple amino groups introduced by Y, and X at the end where m is 0 or n is 0 is methoxy; or
when both m and n are 0, both r and s are 1, artesunate via carboxyl forms an ester or an amide with X.

2. The artesunate-polyethylene glycol derivative according to claim 1, wherein Y is L-lysine, L-ornithine, 2,3-diaminopropionic acid, or 2,4-diaminobutyric acid.

3. The artesunate-polyethylene glycol derivative according to claim 1, wherein the polyethylene glycol residue has a molecular weight of 2,000 to 40,000.

4. The artesunate-polyethylene glycol derivative according to claim 1, which is shown in Formula (II), (II)

wherein, POLY and X are defined as claim 1.

5. The artesunate-polyethylene glycol derivative according to claim 4, which is [(Artesunate -)$_2$-Lys-]$_2$-PEG$_{20k}$, wherein PEG$_{20k}$ represents PEG with molecular weight of 20 kD.

6. The artesunate-polyethylene glycol derivative according to claim 1, which is shown in Formula (III), wherein, POLY, Y, m and s are defined as claim 1, and n is 0, m is not 0.

7. The artesunate-polyethylene glycol derivative according to claim 6, which is:
mPEG$_{20k}$-Lys-(Artesunate)$_2$, wherein mPEG$_{20k}$ represents mono-methoxy PEG with molecular weight of 20 kD.

8. The artesunate-polyethylene glycol derivative according to claim 1, which is shown in Formula (IV), wherein, POLY and X are defined as claim 1, and m and n are both 0.

9. The artesunate-polyethylene glycol derivative according to claim 8, which is: Artesunate-NH-PEG$_{20k}$-NH-Artesunate, wherein, PEG$_{20k}$ represents PEG with molecular weight of 20 kD.

10. A method for preparing the artesunate-polyethylene glycol derivative according to claim 1, comprising the following steps:
placing artesunate and a multivalent polyethylene glycol modifier with free amino groups in an inert solvent, performing a coupling reaction between a carboxyl of artesunate and an amino or hydroxyl of multivalent polyethylene glycol modifier in the presence of catalysis of a coupling agent and an organic alkali.

11. The preparation method according to claim 10, characterized in any one or more of the following items:
(1) the polyethylene glycol modifier is mPEG$_{20k}$ or [Lys-]$_2$-PEG$_{20k}$;
(2) the inert solvent is selected from dichloromethane, chloroform, toluene, or dimethylformamide (DMF);
(3) the coupling agent is selected from N-ethyl-N'-(3-dimethylaminopropyl)carbodiimide hydrochloride (EDC), 1,3-diisopropylcarbodiimide (DIC), N,N-dicyclohexylcarbodiimide (DCC);
(4) the reaction temperature is controlled at 0-25° C.;
(5) the organic alkali is selected from the group consisting of pyridine, triethylamine and diisopropylethylamine.

12. A pharmaceutical composition, which comprises the artesunate-polyethylene glycol derivative according to claim 1; optionally, further comprises a pharmaceutically acceptable carrier or excipient.

13. A method for combating plasmodium in vivo or in vitro, comprising a step of administering to a subject in need thereof an effective amount of the artesunate-polyethylene glycol derivative according to claim 1.

14. A method for prophylaxis and/or treatment of a disease caused by a plasmodium, comprising a step of administering to a subject in need thereof an effective amount of the artesunate-polyethylene glycol derivative according to claim 1.

15. The method according to claim 14, wherein said disease is malaria.

16. An artesunate-polyethylene glycol derivative, which is:

mPEG20k-Lys$_3$-(Artesunate)$_4$, wherein, mPEG20k represents mono-methoxy PEG with molecular weight of 20 kD.

17. A pharmaceutical composition, which comprises the artesunate-polyethylene glycol derivative according to claim 16; optionally, further comprises a pharmaceutically acceptable carrier or excipient.

18. A method for combating plasmodium in vivo or in vitro, comprising a step of administering to a subject in need thereof an effective amount of the artesunate-polyethylene glycol derivative according to claim 16.

19. A method for prophylaxis and/or treatment of a disease caused by a plasmodium, comprising a step of administering to a subject in need thereof an effective amount of the artesunate-polyethylene glycol derivative according to claim 16.

20. The method according to claim 19, wherein said disease is malaria.

* * * * *